United States Patent
Van Belzen et al.

(10) Patent No.: US 11,993,557 B2
(45) Date of Patent: May 28, 2024

(54) METHOD AND REACTOR FOR PRODUCING UREA AMMONIUM SULPHATE

(71) Applicant: YARA INTERNATIONAL ASA, Oslo (NO)

(72) Inventors: Ruud Van Belzen, HJ Sluiskil (NL); Howard Volke, HJ Sluiskil (NL); Erika Winne, Ghent (BE)

(73) Assignee: YARA INTERNATIONAL ASA, Oslo (NO)

( * ) Notice: Subject to any disclaimer, the term of this patent is extended or adjusted under 35 U.S.C. 154(b) by 812 days.

(21) Appl. No.: 16/982,242

(22) PCT Filed: Mar. 20, 2019

(86) PCT No.: PCT/EP2019/056936
§ 371 (c)(1),
(2) Date: Sep. 18, 2020

(87) PCT Pub. No.: WO2019/180066
PCT Pub. Date: Sep. 26, 2019

(65) Prior Publication Data
US 2021/0155582 A1    May 27, 2021

(30) Foreign Application Priority Data

Mar. 20, 2018   (EP) .................................... 18162813

(51) Int. Cl.
*C07C 273/02*   (2006.01)
*B01J 8/06*    (2006.01)
(Continued)

(52) U.S. Cl.
CPC .............. *C07C 273/02* (2013.01); *B01J 8/06* (2013.01); *B01J 19/242* (2013.01); *C01C 1/242* (2013.01);
(Continued)

(58) Field of Classification Search
None
See application file for complete search history.

(56) References Cited

U.S. PATENT DOCUMENTS 3,464,809 A * 9/1969 Hicks ..................... C01C 1/242
                                                            71/61
4,500,336 A    2/1985 Van Hijfte et al.
(Continued)

FOREIGN PATENT DOCUMENTS

CN         101006011 A    7/2007
CN         101132988 A    2/2008
(Continued)

OTHER PUBLICATIONS

Chinese Office Action (including English translation) issued in App. No. CN201980019768.4, dated Oct. 10, 2022, 21 pages.
(Continued)

*Primary Examiner* — Amy C Bonaparte
(74) *Attorney, Agent, or Firm* — Dilworth IP, LLC

(57) ABSTRACT

A method for the production of a urea ammonium sulphate (UAS) composition in a pipe reactor comprising at least a reactor section, the method comprising:
  combining in the reactor continuous feeds of at least one of sulphuric acid and ammonium bisulphate, at least one of ammonia and ammonium carbamate, and urea; and
  including a viscosity-reducing agent selected from water soluble aluminum salts in at least one of the continuous feeds, thereby forming the urea ammonium sulphate (UAS composition, wherein the UAS composition comprises 1 to 40 weight % of ammonium sulphate (AS) relative to the total weight of the UAS composition.

19 Claims, 4 Drawing Sheets

(51) Int. Cl.
*B01J 19/24* (2006.01)
*C01C 1/242* (2006.01)
*C07C 275/02* (2006.01)

(52) U.S. Cl.
CPC ..... *B01J 2219/0004* (2013.01); *C07C 275/02* (2013.01)

(56) References Cited

U.S. PATENT DOCUMENTS

| | | | |
|---|---|---|---|
| 6,179,893 B1* | 1/2001 | Bendix | C05C 3/00 71/30 |
| 2005/0039508 A1 | 2/2005 | Burnham | |
| 2008/0145283 A1* | 6/2008 | Ledoux | C05C 3/00 422/600 |
| 2010/0288003 A1 | 11/2010 | Burnham et al. | |
| 2017/0210675 A1 | 7/2017 | Allais et al. | |
| 2017/0219675 A1 | 8/2017 | Walsh | |

FOREIGN PATENT DOCUMENTS

| | | | |
|---|---|---|---|
| CN | 106470961 A | 3/2017 | |
| DE | 10133935 A1 * | 1/2003 | ............... C05C 3/00 |
| DE | 10133935 A1 | 1/2003 | |
| EP | 0223276 A1 | 5/1987 | |
| EP | 1861335 B1 | 8/2012 | |
| EP | 1781569 B1 | 11/2017 | |
| ES | 2391400 T3 | 11/2012 | |
| RU | 2219146 C1 | 12/2003 | |
| RU | 2373148 C2 | 11/2009 | |
| WO | 8904291 | 5/1989 | |
| WO | 8904291 A1 | 5/1989 | |
| WO | 9521689 A1 | 8/1995 | |
| WO | 0151429 A2 | 7/2001 | |
| WO | 2006093413 A1 | 9/2006 | |
| WO | 2017042194 A1 | 3/2017 | |

OTHER PUBLICATIONS

International Search Report issued in International Application No. PCT/EP2019/056936, dated Jun. 3, 2019, 4 pages.

Russian Office Action (including English translation) issue in App. No. RU2020134407/04, dated Sep. 7, 2022, 13 pages.

Papulov, "Relationship between the properties of substances and molecule structure: mathematical simulation", Advances of Contemporary Natural History, 2006, 4 pages.

* cited by examiner

METHOD AND REACTOR FOR PRODUCING UREA AMMONIUM SULPHATE

TECHNICAL FIELD

The present invention is in the field of urea ammonium sulphate, more particularly, methods and devices for producing urea ammonium sulphate.

BACKGROUND

Urea ammonium sulphate (UAS) is a common fertilizer. UAS is synthesised in solution (up to about 11 weight % of ammonium sulphate (AS) can be dissolved into a urea melt) or in slurry (when a urea melt comprises more than about 11 weight % of AS) before granulation using a tank type reactor or a pipe reactor (see e.g. EP1781569 B1 (Yara International ASA, 2007) and EP1861335 B1 (Yara International ASA, 2007)). However, urea/AS (UAS) slurries or concentrated solutions, comprising urea and ammonium sulphate, have a high viscosity, thus making, e.g. the pumping of these slurries or concentrated solutions in a UAS production process challenging. Adding large amounts of water to a UAS slurry or solution stream in the production process to lower the viscosity is seen as an extra cost since, at some point in the production process, the water needs to be evaporated from said stream, preferably before or during granulation, which requires energy and larger equipment downstream (separator, condenser, scrubber, etc.). Elevating the temperature of the UAS slurry or solution stream to decrease the viscosity is also not preferable as it may otherwise cause decomposition of the UAS or the formation of undesirable by-products, such as biuret. In particular, when using a pipe reactor for the production of UAS, the viscosity of the UAS slurry or solution being formed and/or produced needs to be sufficiency low as otherwise, high pressures are needed to force the melt or concentrated solution through the reactor pipes, orifices and nebulizers of the reactor and of downstream equipment, such as evaporators and granulators. Furthermore, large pressure drops occur in the reactor and/or high wear of the reactor occurs, shortening the life-time of the reactor. Therefore, there is a need to facilitate the formation, processing and handling of UAS slurries or concentrated solutions, especially facilitating the production of UAS slurries or concentrated solutions in a pipe reactor. There is a need to prolong the life-time of a reactor, in particular a pipe reactor. There is a need to lower the viscosity of a UAS slurry or concentrated solution, and such preferably without decomposition of urea, ammonium sulphate or UAS and/or without adding large amounts of water. Most preferably, there is a need to prevent the formation of a high-viscosity UAS slurry or concentrated solution within a pipe reactor when it is forming in the reactor section wherein continuous feeds of sulphuric acid and/or ammonium bisulphate, ammonia and/or ammonium carbamate, and urea are combined to obtain said urea ammonium sulphate (UAS) composition, thereby forming a UAS solution or slurry.

It is one of the objects of the present invention to overcome or ameliorate one or more of the aforementioned disadvantages of the prior art or to answer one of the needs in the field.

SUMMARY

Surprisingly, the present inventors have now found that at least one or more of these objects can be obtained by including, in a process for the production of a urea ammonium sulphate (UAS) composition, wherein said UAS composition comprises 1 to 40 weight % of ammonium sulphate (AS), relative to the total weight of the UAS composition, from sulphuric acid, ammonia and/or ammonium carbamate, and urea, in a pipe reactor comprising at least a reactor section wherein continuous feeds of sulphuric acid and/or ammonium bisulphate, ammonia and/or ammonium carbamate, and urea are combined to obtain said urea ammonium sulphate (UAS) composition, a viscosity-reducing agent, selected from the group of water soluble aluminium salts, into one or more of said feeds, such that the viscosity of said solution or slurry of said urea ammonium sulphate (UAS) is reduced, as compared to a process without adding such viscosity-reducing agent. Accordingly, provided herein are methods and reactors, suitable to add such a viscosity-reducing agent during the production of urea ammonium sulphate (UAS).

It is known in the prior art to add aluminium salts to a urea-ammonium sulphate solution or slurry to reduce the viscosity. DE 101 33 935 (SKW Stickstoffwerke Piesteritz GmbH, 2003) discloses to add a viscosity-reducing compound such as aluminium sulphate, preferably in a concentration of 0.1 to 0.5 weight % relative to the weight of the melt suspension, to a slightly alkaline UAS melt suspension after its production, to lower the viscosity during further process steps of the UAS melt, such as concentration and/or granulation.

It is known in the art to add aluminium salts to a urea-ammonium sulphate solution or slurry in an effort to achieve better granules in terms of hardness, size, granular flowability and long-term storage. U.S. Pat. No. 4,500,336 (Van Hijfte et al., 1985) discloses a 20 weight % suspension of ammonium sulphate in an aqueous urea solution, to which 1 weight % of aluminium sulphate (calculated as the anhydrous salt) was added as a crystallization retarder for spraying on a fluidized bed of urea. EP 02232276 (NSM, 1987) discloses the addition of aluminium sulphate as a crystallization retarder for urea to a melt of urea and ammonium sulphate in an amount of 0.1 to 2 weight % prior to granulation in a fluidized bed. WO89/04291 (Retec Ltd, 1989) discloses a method for the production of ammonium sulphate granules which involves adding a granulating aid, such as aluminium sulphate, to a slurry of ammonia and sulphuric acid. WO 95/21689 (Incitec Ltd, 1995) discloses the use of aluminium sulphate as a granulating aid in the process for making granular urea.

None of the prior art documents discloses the use of aluminium salts as viscosity-reducing agents for preventing the formation of a high-viscosity liquid urea/ammonium sulphate (UAS) composition in a process for the production of a UAS composition in a pipe reactor, in particular during the formation of the UAS in the respective reactor section where sulphuric acid and/or ammonium bisulphate, ammonia and/or ammonium carbamate and urea are combined and reacted.

DESCRIPTION OF THE FIGURES

The following description of the figures of specific embodiments of the invention is only given by way of example and is not intended to limit the present explanation, its application or use. In the drawings, identical reference numerals refer to the same or similar parts and features.

DESCRIPTION OF THE INVENTION

Figure 1:
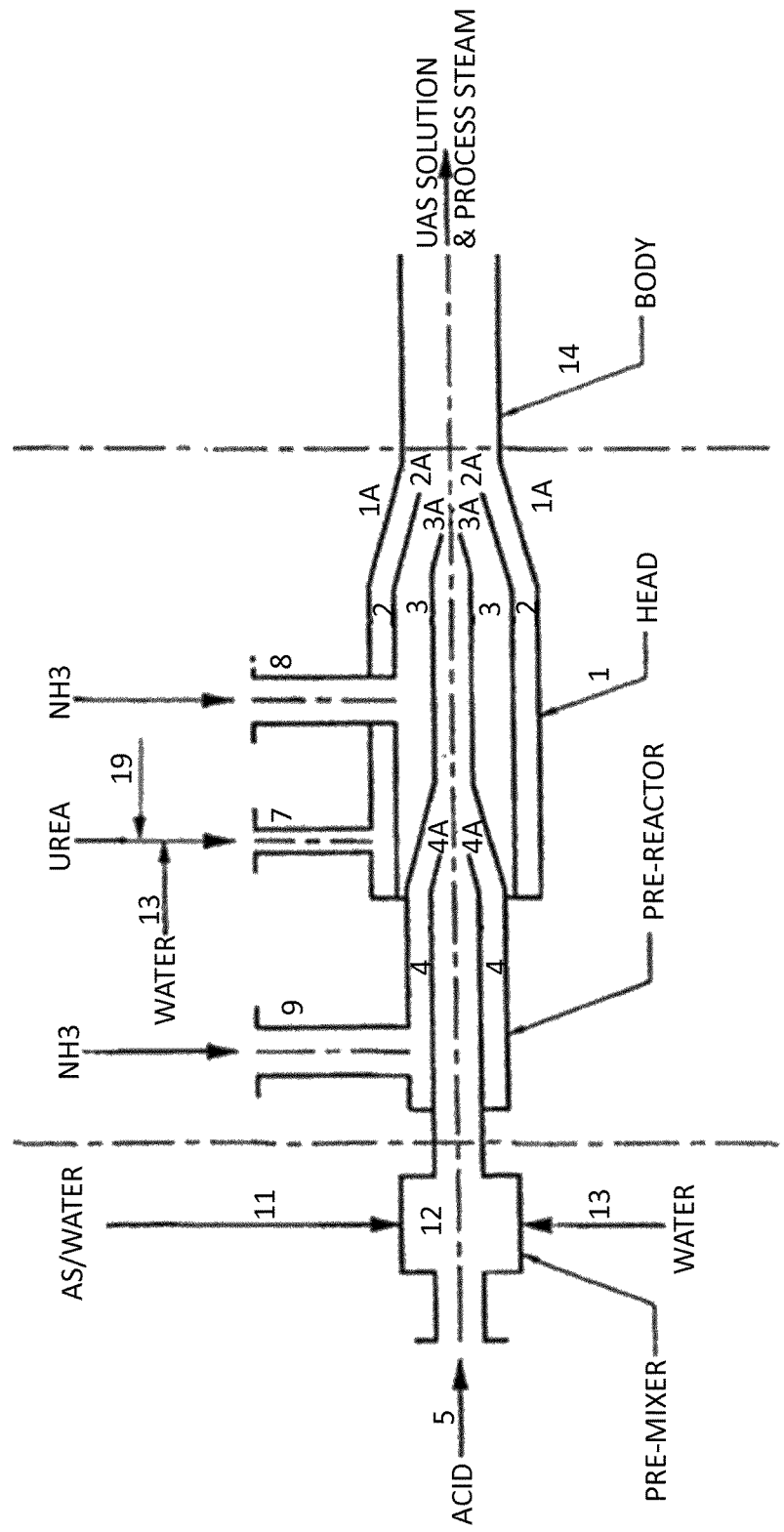
FIG. 1 shows a schematic representation of a double annulus pipe reactor as disclosed in EP 1861335 B1 and EP 1781569 B1, which are both incorporated herein by way of reference, and which pipe reactor may be used in combination with a granulator or any other suitable particularization technology, in a method for producing a solid UAS composition, in particular as disclosed in EP 1781569 B1.

As used below in this text, the singular forms "a", "an", "the" include both the singular and the plural, unless the context clearly indicates otherwise.

The terms "comprise", "comprises" as used below are synonymous with "including", "include" or "contain", "contains" and are inclusive or open and do not exclude additional unmentioned parts, elements or method steps. Where this description refers to a product or process which "comprises" specific features, parts or steps, this refers to the possibility that other features, parts or steps may also be present, but may also refer to embodiments which only contain the listed features, parts or steps.

The enumeration of numeric values by means of ranges of figures comprises all values and fractions in these ranges, as well as the cited end points.

The term "approximately" as used when referring to a measurable value, such as a parameter, an amount, a time period, and the like, is intended to include variations of +/−10% or less, preferably +/−5% or less, more preferably +/−1% or less, and still more preferably +/−0.1% or less, of and from the specified value, in so far as the variations apply to the invention disclosed herein. It should be understood that the value to which the term "approximately" refers per se has also been disclosed.

As used herein, the terms "upstream" and "downstream" are relative to the process stream through a pipe reactor.

All references cited in this description are hereby deemed to be incorporated in their entirety by way of reference.

Unless defined otherwise, all terms disclosed in the invention, including technical and scientific terms, have the meaning which a person skilled in the art usually gives them. For further guidance, definitions are included to further explain terms which are used in the description of the invention.

Method for the Production of a UAS Composition

In its broadest sense, the present disclosure relates a method for the production of a urea ammonium sulphate (UAS) composition, wherein said UAS composition comprises 1 to 40 weight % of ammonium sulphate (AS) relative to the total weight of the UAS composition, from sulphuric acid, ammonia and/or ammonium carbamate, and urea, in a pipe reactor comprising at least a reactor section wherein continuous feeds of sulphuric acid and/or ammonium bisulphate, ammonia and/or ammonium carbamate, and urea are combined to obtain said urea ammonium sulphate (UAS) composition, comprising the step of including a viscosity-reducing agent, selected from the group of water soluble aluminium salts, into one or more of said feeds, such that the viscosity of the urea ammonium sulphate (UAS) solution or slurry, produced in said reactor section, is reduced.

Without being limited to theory, it is theorized that the inclusion of the viscosity-reducing agent in one of the feeds modifies the particle size and/or particle size distribution of the ammonium sulphate particles that are being formed and mixed with urea in the appropriate reactor section, yielding a lower viscosity.

Surprisingly, the inclusion of the viscosity-reducing agent in a feed and exposing the viscosity-reducing agent to the harsh conditions of the reaction in terms of temperature (120 to 200° C.), pressure (1 to 10 bar) and alkalinity (highly alkaline melt), does not deteriorate the composition or quality of a feed nor of the viscosity-reducing agent. This effect and its benefits have never been disclosed nor suggested in the prior art.

Water-soluble aluminium salts can easily be dissolved in the liquid aqueous feeds used in the process, such as the urea feed and the sulphuric acid/ammonium bisulphate feed. According to one embodiment, the viscosity-reducing agent is introduced into a liquid sulphuric acid/ammonium bisulphate feed a liquid urea feed, or a combination thereof. Preferably, the viscosity-reducing agent is introduced into an aqueous feed such as a liquid urea feed. By this aspect of the invention, no extra water is introduced into the reaction mixture that needs to be removed before obtaining the final product.

The viscosity-reducing agent can be introduced continuously or stepwise with a certain frequency to any of the abovementioned feeds. Preferably, the viscosity-reducing agent is added continuously to any one of the abovementioned feeds.

It proved beneficial to select a viscosity-reducing agent that could decrease the viscosity from 1000 to 5000 cp (which is the usual viscosity of such a flow without a viscosity-reducing agent) to a value of 20 to 100 cP, i.e. a reduction with a factor of about 10 to 250. Preferably, the viscosity is reduced to 100 cp, preferably 50 cp, most preferably 20 cp. The viscosity is preferably measured on the UAS product obtained after the separator step, i.e. before any concentration of granulation step.

According to one embodiment, the viscosity-reducing agent is an aluminium sulphate (AluS). AluS is highly soluble in water (31.2 g/100 mL (at 0° C.), 36.4 g/100 mL (at 20° C.) and 89.0 g/100 mL (at 100° C.). Therefore, high concentrations of AluS in water can be achieved. Hence, according to one embodiment, said aluminium salt, in particular aluminium sulphate, is added to a feed as an aqueous solution. Adding an aqueous solution at this point in the process is beneficial as water is part of the UAS-process and no alien solvents are introduced that need to be removed downstream in the process. Also, the amount of water will be small compared to the water already added via the urea feed and above all, any added water is removed by default in the separator, directly after the reactor section wherein continuous feeds of sulphuric acid and/or ammonium bisulphate, ammonia and/or ammonium carbamate, and urea are combined to obtain said urea ammonium sulphate (UAS) composition, which is always present in this process. Hence, no extra dilution is caused compared to the prior art where a viscosity-reducing agent is added to a final UAS composition and where the water needs to be removed before concentration and granulation, optionally using additional equipment to remove water, such as an evaporator.

Aluminium sulphate has the chemical formula $Al_2(SO_4)_3$. Aluminium sulphate is rarely, if ever, encountered as the anhydrous salt. It forms a number of different hydrates, of which the hexadecahydrate $Al_2(SO_4)_3 \cdot 16H_2O$ and octadecahydrate $Al_2(SO_4)_3 \cdot 18H_2O$ are the most common. The heptadecahydrate $Al_2(SO_4)_3 \cdot 17H_2O$ occurs naturally as the mineral alunogen. Aluminium sulphate is sometimes called alum or papermaker's alum in certain industries. However, the name "alum" is more commonly and properly used for any double sulphate salt with the generic formula $XAl(SO_4)_2 \cdot 12H_2O$, where X is a monovalent cation such as potassium or ammonium. Within the context of this application, aluminium sulphate is to comprise all of the above chemical forms and its content is calculated and expressed as $Al_2O_3$. From experiments, it was shown that, after adding a solution of aluminium sulphate in a urea feed prior to the introduction of said feed in a pipe reactor, the amount of soluble aluminum sulfate in the feed produced by the pipe reactor was higher (77% of total amount added) than in the case where the aluminium sulphate is introduced directly in a slurry of UAS (40% of total amount added was solubilized) and to bring about the viscosity-reducing effect, it is necessary to maximize the amount of soluble viscosity-reducing agent in a feed or a product.

According to one embodiment, the viscosity-reducing agent, when it is an aluminium sulphate, is produced on site from aluminium trihydrate and sulfuric acid, the latter of which ingredients is available for the production of ammonium sulphate.

According to one embodiment, the concentration of the aluminium salt, in particular AluS, in the aqueous solution is 5 to 70 weight %, preferably 10 to 60 weight %, more preferably 15 to 50 weight %, even more preferably 20 to 40 weight %, and most preferably 25 to 30 weight %, such as 27 weight % of an aluminium salt, in particular AluS, all weight % relative of the total weight of the aqueous solution.

According to one embodiment, at most 1.0 weight % of an aluminium salt, in particular AluS, and preferably 0.1 to 1 weight %, more preferably 0.2 to 0.9 weight %, even more preferably 0.3 to 0.8 weight %, yet even more preferably 0.4 to 0.7 weight %, and most preferably 0.5 to 0.6 weight % of an aluminium salt, in particular AluS, is present in the UAS composition, all weight % relative to the total weight of the UAS composition (solution or slurry).

To this end, for example, at most 1.1 weight % of an aluminium salt, in particular AluS, and preferably 0.1 to 1.1 weight %, more preferably 0.2 to 1.0 weight %, even more preferably 0.3 to 0.9 weight %, yet even more preferably 0.4 to 0.8 weight %, and most preferably 0.5 to 0.7 weight % of an aluminium salt, in particular AluS, is introduced into a feed, preferably the liquid urea feed.

According to one embodiment, the UAS composition comprises 1 to 40 weight % AS, preferably 1 to 35 weight %, preferably 3 to 30 weight %, more preferably 5 to 25 weight %, even more preferably 7 to 20 weight %, and most preferably 10 to 15 weight % AS, relative to the total weight of the UAS composition. According to a preferred embodiment, the UAS composition comprises about 23 weight % AS. Such a composition is marketed by Yara International ASA as YaraVera™ AMIDAS™. According to a preferred embodiment, the UAS composition comprises about 32 weight % AS. Such a composition is marketed by Yara International ASA as YaraVera™ UREAS™. The amount of AS in a UAS composition can be tuned to a particular amount by selecting the amounts of sulphuric acid and ammonia that are present in the feeds.

According to one embodiment, the UAS composition comprises:
  from at least 0.1 to at most 1 weight % aluminium sulphate;
  from at least 1 to at most 35 weight % AS; and
  from at least 64 to at most 98.9 weight % urea;
wherein all weight % are based on the total weight of the UAS composition.

According to one embodiment, the reactor is a double annulus pipe reactor, as described below. Using such a pipe reactor it is possible to produce urea ammonium sulphate (UAS) from feeds of sulphuric acid and ammonium bisulphate, ammonia and/or ammonium carbamate, and urea without substantially decomposing urea.

According to one embodiment, the present invention relates a method for the production of a urea ammonium sulphate (UAS) from sulphuric acid, ammonia and/or ammonium carbamate, and urea, in a pipe reactor comprising at least a reactor section wherein feeds of sulphuric acid and/or ammonium bisulphate, ammonia and/or ammonium carbamate, and urea are combined, to obtain said urea ammonium sulphate (UAS), comprising the steps of:
  a) providing sulphuric acid and/or ammonium bisulphate and ammonia and/or ammonium carbamate to a first reactor section;
  b) in said first reactor section, reacting at least part of said sulphuric acid and/or ammonium bisulphate and at least part of said ammonia and/or ammonium carbamate into ammonium sulphate (AS);
  c) providing a urea solution to a second reactor section; and
  d) mixing said feed resulting from step b) with said urea solution provided in step c) in a third reactor section in the presence of ammonia and/or ammonium carbamate, thereby forming a UAS solution or slurry;
  wherein a viscosity-reducing agent, selected from the group of water soluble aluminium salts, is included into said urea solution prior to step c), such that the viscosity of said UAS solution or slurry, resulting from step d) is reduced, as compared to a process without adding said viscosity-reducing to said urea solution prior to step c).

It was found that the claimed inclusion of the viscosity-reducing agent to said urea solution viscosity-reducing is beneficial over the addition of the viscosity-reducing agent at other points of introduction, such as through a separate addition line to a UAS flow anywhere in the process. The addition of the viscosity-reducing agent had no influence on the characteristics of the urea or its flow, or on the UAS process as a whole, except for the viscosity-reducing effect.

In particular, said viscosity-reducing agent is an aluminium sulphate (AluS), in particular selected from the group of anhydrous, hexadecahydrate, heptadecahydrate and octadecahydrate aluminium sulphate, and a double sulphate salt with the generic formula $XAl(SO_4)_2 \cdot 12H_2O$, where X is a monovalent cation, and mixtures thereof According to the invention, the viscosity-reducing agent, in particular AluS, is added to the urea solution feed before the urea solution is added to the second reactor part. This way, the AluS is present in the composition before the UAS starts to form, starting the viscosity-reducing effect from the moment UAS starts to form.

The addition of a viscosity-reducing agent to UAS solutions or UAS slurries makes the handling and the concentration by evaporation of UAS solutions or UAS slurry easier. Providing the UAS solution or UAS slurry to a granulator will be easier and/or faster, as less pressure is needed to move the less viscous UAS solution or UAS slurry. Because the UAS solution or UAS slurry is less viscous, less wear will occur in the reactor, prolonging the life-time of the reactor and of equipment placed in the reactor. This also results in less downtime due to maintenance. Especially a pipe reactor requires low viscosities such that less pressure needs to be applied to force the UAS solution or UAS slurry through the reactor. The lower viscosity results in a smaller pressure drop over the reactor. The addition of the viscosity-reducing agent, in particular AluS, lowers the viscosity of the UAS solution or UAS slurry and avoids the addition of large amounts of water that need to be evaporated downstream of the reactor. It also avoids the need to heat up the UAS solution or UAS slurry to higher temperatures to lower the viscosity, resulting in the at least partial decomposition of the UAS.

Pipe Reactor

The invention further relates to a pipe reactor for the production of a urea ammonium sulphate (UAS) composition wherein said UAS comprises 1 to 40 weight % of ammonium sulphate (AS) relative to the total weight of the UAS composition, from sulphuric acid, ammonia and/or ammonium carbamate and urea, the pipe reactor comprising at least a reactor section wherein continuous feeds of sulphuric acid and/or ammonium bisulphate, ammonia and/or ammonium carbamate and urea are combined to obtain said urea ammonium sulphate (UAS) composition, wherein the pipe reactor further comprises means for supplying an aqueous solution of a viscosity-reducing agent to the urea solution upstream of the pipe reactor section where said urea solution is mixed with ammonium sulphate to produce a UAS solution or slurry, which agent reduces the viscosity of said UAS solution or slurry.

In particular, the pipe reactor is a pipe reactor as disclosed in EP 1861335 B1 and EP 1781569 B1, which are both incorporated herein by way of reference, and which may be used in combination with a granulator, in a method for producing a solid UAS composition, in particular as disclosed in EP 1781569 B1. The use of a pipe reactor allows for the production process to be a continuous process, with relative short retention time in the reactor, resulting in less decomposition. Further advantages are a high degree of mixing, flexible in operation, low investment cost, low static loads on the building structure and/or easy to replace when corroded. The continuous process also makes it easy to couple the reactor to an on-site continuous process for one or more of the starting materials such as ammonia and/or ammonium carbamate or urea.

In particular, the pipe reactor comprises a tubular body and a reactor head, wherein the reactor head comprises (i) means for axial injection of sulphuric acid, (ii) means for injection of ammonia and/or ammonium carbamate, (iii) means for supplying a urea solution; and (iv) a reaction chamber, wherein the means for axial injection of sulphuric acid has a first cone, the means for injection of ammonia and/or ammonium carbamate comprises an inlet, has a second cone at its downstream end, and forms a first annular chamber surrounding the means for injection of sulphuric acid, the means for supplying a urea solution comprises an inlet, has a convergent part at its downstream end, and forms a second annular chamber surrounding the means for injection of ammonia and/or ammonium carbamate; and the reactor chamber is substantially formed by the zone between the end of first cone and the end of the second cone, wherein the pipe reactor further comprises means for supplying an aqueous solution of a viscosity-reducing agent to the urea solution.

In particular, means for supplying an aqueous solution of a viscosity-reducing agent to the urea solution comprises a pump that is able to introduce said aqueous solution to a feed line pressured at 1 to 10 bar and held at 90-150° C.

In particular, said viscosity-reducing agent is an aluminium sulphate (AluS), in particular selected from the group of anhydrous, hexadecahydrate, heptadecahydrate and octadecahydrate aluminium sulphate, and a double sulphate salt with the generic formula $XAl(SO_4)_2 \cdot 12H_2O$, where X is a monovalent cation, and mixtures thereof.

According to one embodiment, a pre-reactor for (partly) pre-neutralizing the sulphuric acid is arranged upstream of the reactor head. With pre-neutralizing the sulphuric acid is meant in the context of this disclosure that the sulphuric acid is partly converted into ammonium bisulphate. Ammonium bisulphate corresponds to the product made by reacting one mole of sulphuric acid with one mole of ammonia, whereas ammonium sulphate corresponds to the product made by reacting one mole of sulphuric acid with two moles of ammonia. The first ammoniation of sulphuric acid (leading to ammonium bisulphate) is more exothermic than the second one. Hence, ammonium bisulphate is much less aggressive to urea than sulphuric acid, thus limiting urea losses and it has a far higher solubility in water than ammonium sulphate, thus prevention blockage of the pipe reactor. To achieve such partly pre-neutralization, non-equimolar amounts of ammonia and sulphuric acid are introduced into the pre-reactor. To achieve a complete pre-neutralization, equimolar amounts of ammonia and sulphuric acid are introduced into the pre-reactor.

According to one embodiment, the pre-reactor may be a pipe reactor itself.

According to one embodiment, the pre-reactor is part of the main pipe reactor, and the means for injection of ammonia and or ammonium carbamate comprise an inlet.

According to one embodiment, a pre-mixer for dilution of the sulphuric acid is arranged upstream of the reactor head. The pre-mixer can be used on the sulphuric acid line to dilute the sulphuric acid with an aqueous solution. Advantageously, the viscosity-reducing agent is included into such aqueous solution.

Plant for the Manufacture of Urea Ammonium Sulphate

The invention also concerns a plant for the manufacture of urea ammonium sulphate comprising a pipe reactor according to the invention, which is designed for the production of a urea ammonium sulphate (UAS) composition from sulphuric acid, ammonia and/or ammonium carbamate and urea, without substantially decomposing urea.

According to one embodiment, the plant further comprises a pre-reactor for (partly) pre-neutralizing the sulphuric acid to ammonium bisulphate, a pre-mixer for dilution of the sulphuric acid upstream of the reactor head, a separator, such as a separator tank, to separate steam produced from the UAS slurry, and means for receiving the steam.

According to one embodiment, the reactor head is preceded by a pre-reactor, which has means for injection of ammonia, means for supply of sulphuric acid and a reaction chamber.

According to one embodiment, a pre-mixer for dilution of the sulphuric acid can be arranged upstream of the reactor head.

According to one embodiment, a flash tank could follow the separator: to limit the high temperature, which enhances the unwanted decomposition of urea, as well as to achieve the right water content for the UAS-solution to be e.g. sprayed into a fluidised bed granulator (typically about 2 to 5 weight % water), the UAS-solution is preferably flashed under vacuum. The flashing can be directly performed in the pipe reactor separator or in a second vessel, so called a flash tank. Use of such a flash tank avoids overdesigning the vacuum system (condenser and non-condensables extraction) but requires doubling the process steam scrubber and the condensing system, in case the steam from the separator is to be condensed. Therefore, this configuration of a separator plus a flash tank has to be studied case by case and is anyway very advisable in case of high plant capacity and consumption of urea plant off gas ammonia with involvement of large amount of non-condensables (such as $CO_2$ released by ammonium carbamate decomposition). The steam produced in the reactor and separated in the separator contains mainly steam, but also some unreacted ammonia, carbon dioxide, some air, as well as droplets of UAS-solution. Various non-condensables (NOx, SOx, ...) may be present in negligible amounts, depending on the quality of the entrants, not significantly created in the reactor.

According to one embodiment, the means for receiving the steam are preferably a scrubber that could be designed in two distinct stages. The scrubber preferably has means for recycling scrubbing solution to the urea inlet and/or to the sulphuric acid injector. According to one embodiment, the scrubber is a wet scrubber. The droplets of solution are caught within the scrubbing solution. The scrubber is partially acidified with sulphuric acid, to also stop the ammonia. The scrubber is preferably designed in two distinct stages: in the first one the droplets of urea are stopped by a quite neutral scrubbing solution, while the second step is acidic to catch the ammonia. It avoids enhancing urea degradation by strongly acidifying a urea containing scrubbing solution. If the scrubber is designed in two distinct stages, then the scrubbing solution from the second stage is preferably systematically recycled into the sulphuric acid line feeding the reactor, because this solution is nearly free of urea. Urea containing scrubbing solutions from the first stage should preferably not be recycled directly in the sulphuric acid to avoid high rate of degradation of urea. This solution can be mixed with the scrubbing solution from the granulation section and sent to the urea solution feeding the pipe reactor. Alternatively, the solution can be recycled to the urea concentration section, be exported or can be used as make up water in the scrubber of the granulation section.

The production of ammonium urea sulphate is preferably a tail end process of a urea plant.

EXPERIMENTAL

The invention will now be elucidated by reference to FIGS. 1 to 4.

FIG. 1 shows a pipe reactor preceded by a pre-mixer and a pre-reactor. The reactor head (1) and reactor body (14) of the pipe reactor is compulsory in all variations of the reactor, while the use of a pre-mixer and pre-reactor will be dependent on the process conditions.

The head (1) of the reactor comprises a reaction chamber. This is the zone comprised between the end of the sulphuric acid cone (3A) and the end of the ammonia cone (2A), where ammonia and/or ammonia carbamate and (partly neutralized) sulphuric acid come into contact with each other and react. The head (1) is tubular with a convergent part (1A) at its downstream end. It has an axial sulphuric acid injector (3, 3A) through which a composition comprising mainly (partly neutralised) sulphuric acid is axially injected in the pipe reactor. Ammonia and/or ammonium carbamate is introduced tangentially through inlet (8) into an ammonia injector (2) forming a first annular chamber surrounding the acid injector (3, 3A). The ammonia injector (2) has a cone (2A) at its downstream end. An aqueous composition comprising mainly urea (optionally together with other components such as formaldehyde, biuret, ammonium sulphate and ammonia) is supplied through an inlet (7) to a second annular chamber surrounding the ammonia injector (2). The body (14) of the reactor is the straight length of the reactor downstream of the convergent part (1A). The viscosity-reducing agent which reduces the viscosity of the UAS solution or slurry is added through an inlet (19), which is arranged upstream of the inlet (7). Preferably, the viscosity-reducing agent is added continuously to the aqueous urea composition.

According to the presented embodiment, sulphuric acid is partially neutralized by ammonia before any introduction of urea, in a separate reactor, hereafter called a pre-reactor. The pre-reactor is arranged upstream of the reactor head (1) of a pipe reactor and has an inlet (9) for ammonia and/or ammonium carbamate to an annular chamber surrounding the axial sulphuric acid supply wherein the acid injector (4) has a conical end (4A). Hence, three distinct flows enter the pipe reactor, which flows can be described as a double annulus flow: the (partly neutralised) sulphuric acid flow is in the centre, the ammonia and/or ammonium carbamate flow is in the first, inner, annulus, and the flow of urea to which the viscosity-reducing agent has been added, is in the second, outer, annulus. Such a pipe reactor is called a double annulus pipe reactor.

A pre-mixer (12) is arranged upstream of the pre-reactor and can be used on the sulphuric acid line to dilute the sulphuric acid flow (5) with water (13) or with scrubbing solution (11) from a scrubbing section, comprising mainly water and ammonium sulphate.

Not illustrated is a double stage scrubbing wherein a first stage is catching urea and a second stage is acidified using an acid flow to catch ammonia and convert it into ammonium sulphate, which can be recycled into the process.

Figure 2:
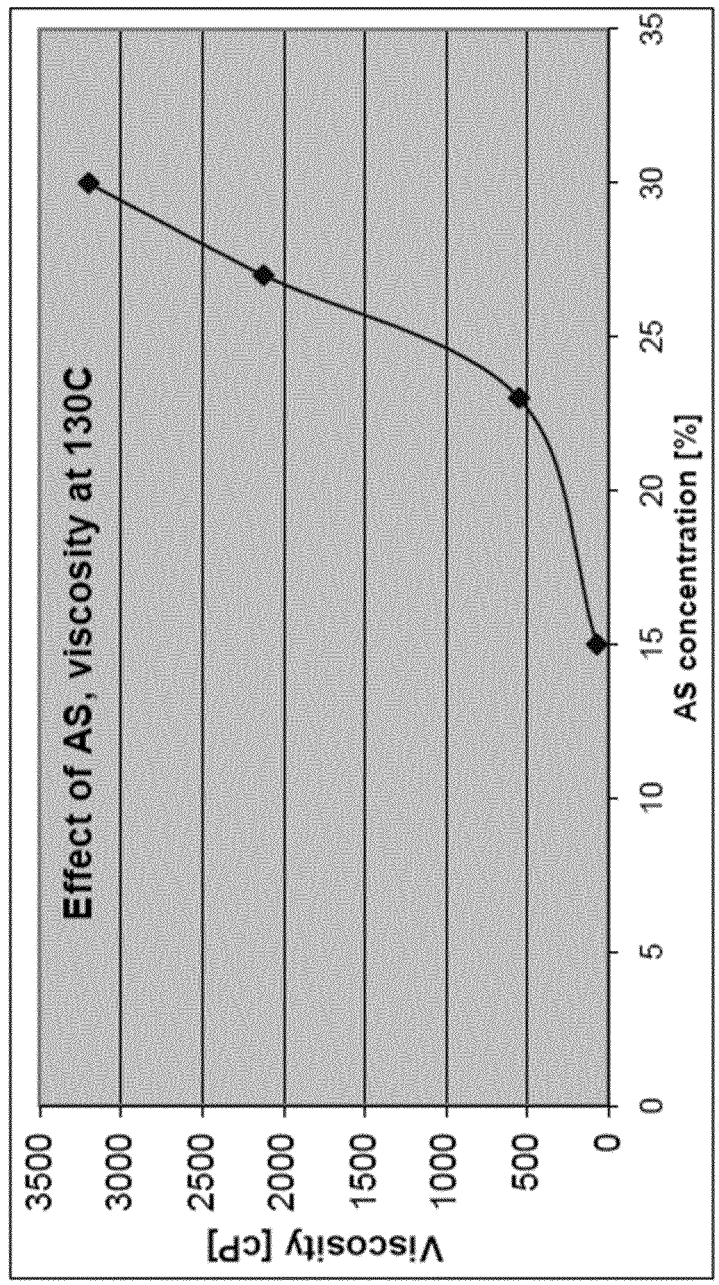
FIG. 2 shows the viscosity profile for a mixture of urea and ammonium sulphate and its effect on the addition of increasing amounts of ammonium sulphate to a urea solution.

The effect of the addition of ammonium sulphate to a urea melt is shown in FIG. 2. From a AS concentration of about 23 weight %, the viscosity steeply rises, giving rise to a slurry which is very hard to transport.

Figure 3:
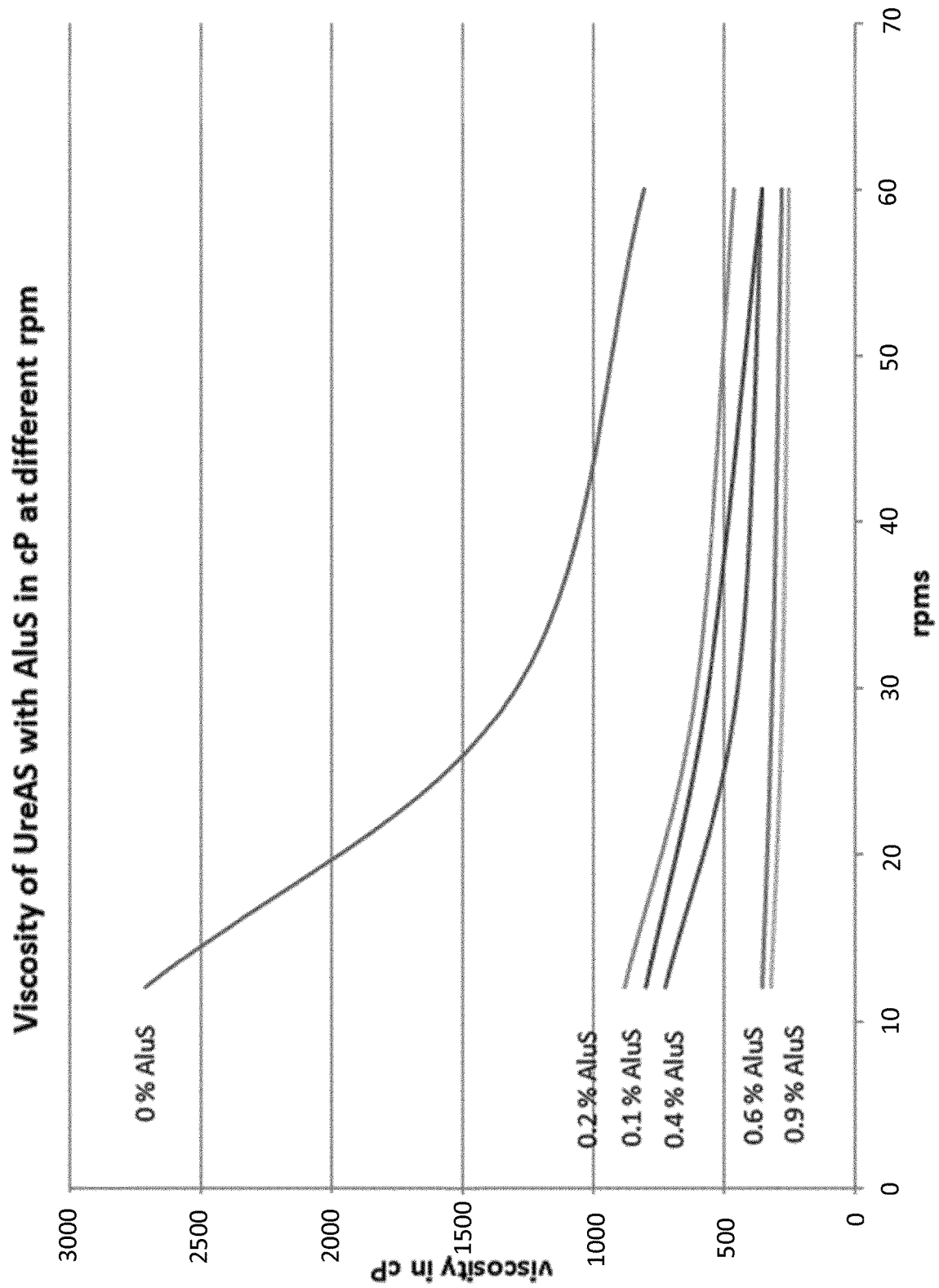
FIG. 3 shows the viscosity of a urea ammonium sulphate (UAS) composition with different amounts of aluminium sulphate added at different rpm, produced according to the invention.

The effect of the addition of aluminium sulphate on the viscosity of a UAS composition which comprises 32 weight % AS (marketed by Yara International ASA as Ureas©) is shown in FIG. 3. It is remarkable that an amount as small as 0.1 weight % of aluminium sulphate induces a dramatic decrease of the viscosity, which can be reduced further by adding up to 0.6 weight % of aluminium sulphate. The addition of more than 1 weight % of aluminium sulphate does not seem to decrease the viscosity much.

Figure 4:
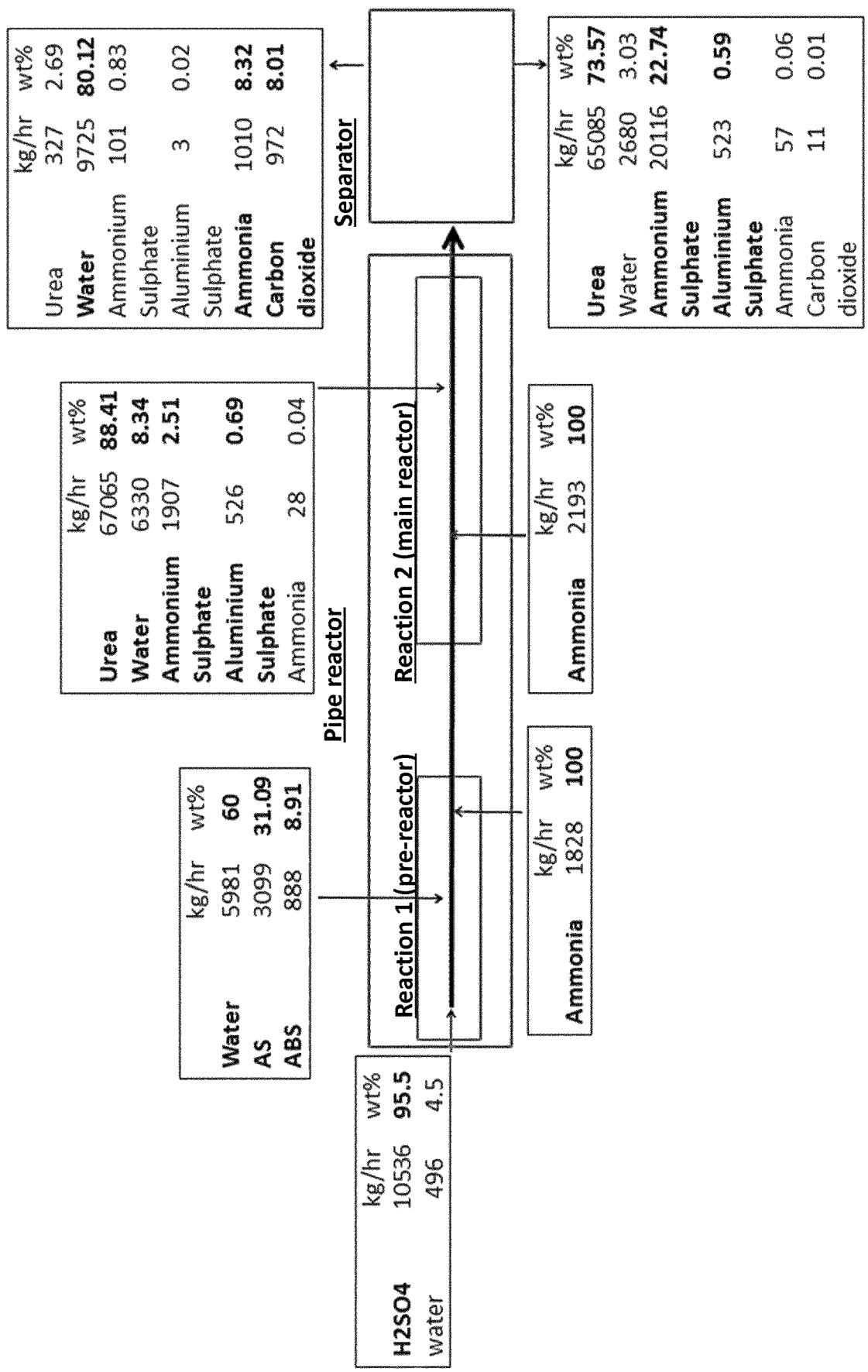
FIG. 4 shows a mass balance for the production of a UAS-composition comprising 23 weight % AS using the double annulus pipe reactor according to FIG. 1. Such a composition is marketed by Yara International ASA as YaraVera™ AMIDAS™.

FIG. 4 shows the mass balance for the production of an UAS-composition comprising 23 weight % AS using 0.69 weight % of aluminium sulphate (relative to the weight of the urea feed), premixed with the urea. Such a composition is marketed by Yara International ASA as YaraVera™ AMIDAS™. It could not have been produced effectively without the viscosity-reducing agent as without the viscosity-reducing agent, the pipe reactor would produce melts that are difficult to transport, pump and handle downstream of the pipe reactor.

The invention claimed is:

1. A method for the production of a urea ammonium sulphate (UAS) composition in a pipe reactor comprising at least a reactor section, the method comprising:

combining in the reactor continuous feeds of at least one of sulphuric acid and ammonium bisulphate, at least one of ammonia and ammonium carbamate, and urea; and including a viscosity-reducing agent selected from water soluble aluminum salts in at least one of the continuous feeds, thereby forming the urea ammonium sulphate (UAS) composition, wherein the UAS composition comprises 1 to 40 weight % of ammonium sulphate (AS) relative to the total weight of the UAS composition.

2. The method according to claim 1, wherein the viscosity-reducing agent is included in the urea feed, wherein the urea feed is liquid.

3. The method according to claim 1, wherein the viscosity-reducing agent is included into the at least one of the ammonia and ammonium carbamate feed.

4. The method according to claim 1, wherein the viscosity-reducing agent is included in the at least one of the sulphuric acid and ammonium bisulphate feeds, wherein the sulphuric acid is a liquid.

5. The method according to claim 1, wherein said viscosity-reducing agent reduces the viscosity of the urea ammonium sulphate (UAS) composition by a factor of about 10 to 250, wherein the composition is in the form of a solution or slurry.

6. The method according to claim 1, wherein the viscosity of the urea ammonium sulphate (UAS) composition is in the form of a solution or slurry, and is reduced to 100 cp.

7. The method according to claim 1, wherein said viscosity-reducing agent is an aluminium sulphate (AluS).

8. The method according to claim 1, wherein said aluminium salt is added to a feed as an aqueous solution.

9. The method according to claim 8, wherein the concentration of said aluminium salt in the aqueous solution is 5 to 70 weight %, relative to the total weight of the aqueous solution.

10. The method according to claim 1, wherein 0.1 to 1 weight % of said aluminium salt, relative to the total weight of the UAS composition, is present in the UAS composition.

11. The method according to claim 1, wherein the UAS composition comprises about 23 weight % AS, or about 32 weight % AS, relative to the total weight of the UAS composition.

12. The method according to claim 1, wherein said UAS composition comprises from at least 0.1 to at most 1 weight % aluminium sulphate, from at least 1 to at most 35 weight % AS, and from at least 64 to at most 98.9 weight % urea, wherein all weight % are based on the total weight of the UAS composition.

13. The method according to claim 1, wherein the reactor is a double annulus pipe reactor.

14. The method according to claim 1 for the production of the urea ammonium sulphate (UAS) composition, further comprising:

a) providing the sulphuric acid and/or the ammonium bisulphate and the ammonia and/or the ammonium carbamate to a first reactor section;

b) reacting in the first reactor section at least part of the sulphuric acid and/or the ammonium bisulphate and at least part of the ammonia and/or the ammonium carbamate into the ammonium sulphate (AS);

c) providing a urea solution to a second reactor section; and d) mixing the feed resulting from step b) with the urea solution provided in step c) in a third reactor section in the presence of the ammonia and/or the ammonium carbamate, thereby forming a UAS solution or slurry;

wherein the viscosity-reducing agent is included in the urea solution prior to step c).

15. A method for the production of urea ammonium sulphate in a pipe reactor comprising at least a reactor section wherein continuous feeds of at least one of sulphuric acid and ammonium bisulphate, at least one of ammonia and ammonium carbamate, and urea are combined to obtain said urea ammonium sulphate (UAS) composition, wherein the pipe reactor further comprises a means for supplying an aqueous solution of a viscosity-reducing agent to the urea solution upstream of the pipe reactor section, which agent reduces the viscosity of the UAS composition, wherein the composition is in the form of a solution or slurry the method comprising:

axially injecting the feed of the at least one of sulphuric acid and ammonium bisulphate into the pipe reactor;

injecting the at least one of the ammonia and ammonium carbamate into the pipe reactor;

supplying the urea solution to the pipe reactor; and supplying the aqueous solution of the viscosity-reducing agent to the urea solution, upstream of the pipe reactor section thereby reducing the viscosity of the UAS solution or slurry.

16. The method according to claim 15, wherein the viscosity-reducing agent supplied to the urea solution is a water-soluble aluminium salt.

17. The method according to claim 6, wherein the viscosity of the urea ammonium sulphate (UAS) solution or slurry is reduced to 50 cp.

18. The method according to claim 17, wherein the viscosity of the urea ammonium sulphate (UAS) solution or slurry is reduced to 20 cp.

19. The method according to claim 7, wherein the aluminum sulphate (AluS) is selected from anhydrous, hexadecahydrate, heptadecahydrate and octadecahydrate aluminium sulphate, a double sulphate salt with the generic formula $XAl(SO_4)_2 \cdot 12\ H_2O$, where X is a monovalent cation, and mixtures thereof.

\* \* \* \* \*